US011918778B2

(12) United States Patent
Imtiaz et al.

(10) Patent No.: US 11,918,778 B2
(45) Date of Patent: Mar. 5, 2024

(54) SMART SELF-ACTIVATING WEARABLE DEVICE FOR AUTOMATICALLY INJECTING MEDICINES

(71) Applicant: Innovative Health Strategies LLC, Peoria, IL (US)

(72) Inventors: Mohammad Shariq Imtiaz, Peoria, IL (US); Charles Vaughn Bandoian, Peoria, IL (US); Thomas Joseph Santoro, Peoria, IL (US)

(73) Assignee: INNOVATIVE HEALTH STRATEGIES LLC, Peoria, IL (US)

( * ) Notice: Subject to any disclaimer, the term of this patent is extended or adjusted under 35 U.S.C. 154(b) by 119 days.

(21) Appl. No.: 17/892,042

(22) Filed: Aug. 19, 2022

(65) Prior Publication Data
US 2023/0140176 A1    May 4, 2023

Related U.S. Application Data

(60) Provisional application No. 63/234,879, filed on Aug. 19, 2021.

(51) Int. Cl.
*A61M 5/14* (2006.01)
*A61M 5/142* (2006.01)
*A61M 5/20* (2006.01)
*A61M 5/168* (2006.01)

(52) U.S. Cl.
CPC .... *A61M 5/14248* (2013.01); *A61M 5/16881* (2013.01); *A61M 5/2053* (2013.01); *A61M 2005/14252* (2013.01); *A61M 2005/206* (2013.01)

(58) Field of Classification Search
CPC ................ A61M 2005/14252; A61M 5/14248
See application file for complete search history.

(56) References Cited

U.S. PATENT DOCUMENTS

| 3,702,609 | A | * | 11/1972 | Steiner | A61M 5/31591 |
| | | | | | 604/139 |
| 4,031,889 | A | | 6/1977 | Pike | |
| 4,233,975 | A | * | 11/1980 | Yerman | A61M 5/286 |
| | | | | | 604/110 |
| 4,886,499 | A | * | 12/1989 | Cirelli | A61M 5/142 |
| | | | | | 604/141 |
| 5,167,632 | A | * | 12/1992 | Eid | A61M 5/2033 |
| | | | | | 604/195 |

(Continued)

FOREIGN PATENT DOCUMENTS

| EP | 1545551 | | 3/2004 |
| GB | 2456245 | A | 7/2009 |
| WO | 2004094823 | A2 | 11/2004 |

OTHER PUBLICATIONS

Search Report and Written Opinion from corresponding PCT application No. PCT/US2022/040971 dated Nov. 21, 2022.

*Primary Examiner* — William R Carpenter
(74) *Attorney, Agent, or Firm* — Porter Wright Morris & Arthur LLP

(57) ABSTRACT

A compact and smart wearable device is configured to automatically inject medicines into the wearer. Because hypodermic needles are only deployed when triggered, infection risks are eliminated. Necessary medicines are automatically deployed based on physiological or other data without human intervention to save lives.

18 Claims, 5 Drawing Sheets

(56) References Cited

U.S. PATENT DOCUMENTS

| | | | | |
|---|---|---|---|---|
| 5,298,024 | A * | 3/1994 | Richmond | A61M 5/31595 |
| | | | | 604/88 |
| 6,045,534 | A * | 4/2000 | Jacobsen | A61N 1/30 |
| | | | | 604/140 |
| 7,637,891 | B2 * | 12/2009 | Wall | A61M 5/422 |
| | | | | 604/93.01 |
| 8,021,349 | B2 * | 9/2011 | Nalesso | A61M 5/284 |
| | | | | 604/167.03 |
| 9,636,460 | B1 | 5/2017 | Jaeger et al. | |
| 2004/0092875 | A1 * | 5/2004 | Kochamba | A61M 37/00 |
| | | | | 604/146 |
| 2004/0116847 | A1 * | 6/2004 | Wall | A61K 9/0021 |
| | | | | 604/93.01 |
| 2007/0233019 | A1 * | 10/2007 | Forsell | A61M 5/14276 |
| | | | | 604/288.03 |
| 2015/0231334 | A1 | 8/2015 | Buchine et al. | |
| 2015/0335817 | A1 | 11/2015 | Lambert | |
| 2017/0246393 | A1 | 8/2017 | Genosar | |
| 2017/0259014 | A1 * | 9/2017 | Nessel | A61M 5/16881 |
| 2019/0269862 | A1 | 9/2019 | Gray | |
| 2020/0164155 | A1 * | 5/2020 | Mojarrad | A61M 5/19 |
| 2021/0386932 | A1 | 12/2021 | Walsh et al. | |
| 2022/0118177 | A1 | 4/2022 | Burgess et al. | |

\* cited by examiner

SMART SELF-ACTIVATING WEARABLE DEVICE FOR AUTOMATICALLY INJECTING MEDICINES

CROSS-REFERENCE TO RELATED APPLICATIONS

This application claims the priority benefit of U.S. Provisional Patent Application No. 63/234,879 filed on Aug. 19, 2021, the disclosure of which is expressly incorporated herein in its entirety by reference.

STATEMENT REGARDING FEDERALLY SPONSORED RESEARCH

Not Applicable

PARTIES TO A JOINT RESEARCH AGREEMENT

Not Applicable

REFERENCE TO APPENDIX

Not Applicable

FIELD OF THE INVENTION

The field of the present invention generally relates to drug delivery systems and, more particularly, to automated drug delivery systems.

BACKGROUND OF THE INVENTION

Catastrophic emergencies are acute medical conditions that require immediate treatment. Such acute medical conditions include, but are not limited to, drug overdose, diabetic coma precipitated by the relative lack of insulin, and anaphylactic shock in response to the bite of an insect to which one harbors a sever allergy. Effective treatment of these acute medical conditions frequently requires the immediate administration of medication needed to mitigate the cardiac, respiratory and/or metabolic consequences of the emergency. Because catastrophic emergencies may occur unwitnessed, evolve rapidly, and/or compromise cognitive as well as physical capacity, the most reliable treatment device should be automatic (i.e. involve no decision making or physical action on the part of the victim), specific (i.e. as selective as possible for the emergent condition), and predictive (i.e. should be triggered by physiological data that reliably predicts an impending catastrophic event).

Currently available automatic drug injection systems typically require embedded cannulas. These cannulas can become unintentionally dislodges or can cause infection. Additionally, currently available automatic drug injection systems also typically require human intervention. Such as, for example, pressing an activation button. Furthermore, currently available drug delivery systems are bulky and unwearable. Even when they are wearable, they are obtrusive and inconvenient to wear.

Accordingly, there is a need for a self-activating drug delivery system that can store and deliver specific medicines for specific conditions on-demand and without human intervention.

SUMMARY OF THE INVENTION

Disclosed are devices and methods which overcome at least some of the above-identified problems of the prior art.

Disclosed is a wearable device for automatically injecting a fluid into a wearer of the wearable device. the wearable device comprises, in combination, an enclosure, an attachment for securing the enclosure to the wearer, at least one injection cylinder within the enclosure, an injection piston within the injection cylinder configured for movement within the injection cylinder, at least one hypodermic needle carried by the injection piston for insertion into the wearer. The injection piston divides the injection cylinder into a first portion containing the fluid to be injected and a second portion containing an insertion end of the at least one hypodermic needle. A valve member is located within the first portion of the injection cylinder containing the fluid to be injected and blocking flow of the fluid to be injected to the at least one hypodermic needle. At least one tether secured to the valve member to limit movement of the valve member so that the valve member permits flow of the fluid to be injected from the injection cylinder above the injection piston to the at least one hypodermic needle when the injection piston moves a distance adequate to insert the at least one hypodermic needle into the wearer.

Also disclosed is a wearable device comprising, in combination, an enclosure including a base portion and top portion closing a top of the base portion, an attachment for securing the enclosure to the wearer, at least one fluid cylinder within the base portion of the enclosure and having an open top closed by the top portion of the enclosure, at least one injection cylinder within the base portion of the enclosure and having an open top closed by the top portion of the enclosure, a fluid piston within the fluid cylinder configured for longitudinal movement within the fluid cylinder, and an injection piston within the injection cylinder configured for longitudinal movement within the injection cylinder, a passage connecting the fluid cylinder above the fluid piston with the injection cylinder above the injection piston, at least one hypodermic needle carried by the injection piston for insertion into the wearer. The injection piston divides the injection cylinder into a first portion containing the fluid to be injected and a second portion containing an insertion end of the at least one hypodermic needle. The fluid piston divides the fluid cylinder into a first portion containing the fluid to be injected and a second portion.

Further disclosed is a wearable device comprising, in combination an enclosure including a base portion, and top portion closing a top of the base portion, an attachment for securing the enclosure to the wearer, at least one fluid cylinder within the base portion of the enclosure and having an open top closed by the top portion of the enclosure, at least one injection cylinder within the base portion of the enclosure and having an open top closed by the top portion of the enclosure, a fluid piston within the fluid cylinder configured for longitudinal movement within the fluid cylinder, an injection piston within the injection cylinder configured for longitudinal movement within the injection cylinder, a passage connecting the fluid cylinder above the fluid piston with the injection cylinder above the injection piston, and at least one hypodermic needle carried by the injection piston for insertion into the wearer. The injection piston divides the injection cylinder into a first portion containing the fluid to be injected and a second portion containing an insertion end of the at least one hypodermic needle. The fluid piston divides the fluid cylinder into a first portion containing the fluid to be injected and a second portion. A valve member is located within the first portion of the injection cylinder containing the fluid to be injected and blocking flow of the fluid to be injected to the at least one hypodermic needle. At least one tether is secured to the valve member to limit movement of the valve member so that the valve member permits flow of the fluid to be injected from the injection cylinder above the injection piston to the at least one hypodermic needle when the injection piston moves a distance adequate to insert the at least one hypodermic needle into the wearer.

From the foregoing disclosures and the following more detailed description of various preferred embodiments it will be apparent to those skilled in the art that the present invention provides a significant advance in the technology and art of automatic drug delivery systems. Particularly significant in this regard is the potential the invention affords for wearable automatic drug injection systems that require no human intervention and are unobtrusive and convenient to wear. Additional features and advantages of various preferred embodiments will be better understood in view of the detailed description provided below.

BRIEF DESCRIPTION OF THE DRAWINGS

These and further features of the present invention will be apparent with reference to the following description and drawing, wherein.

DETAILED DESCRIPTION OF CERTAIN PREFERRED EMBODIMENTS

It will be apparent to those skilled in the art, that is, to those who have knowledge or experience in this area of technology, that many uses and design variations are possible for the wearable devices for injecting medicines and other liquids into wearers disclosed herein. The following detailed discussion of various alternative and preferred embodiments will illustrate the general principles of the invention. Other embodiments suitable for other applications will be apparent to those skilled in the art given the benefit of this disclosure.

Figure 1:
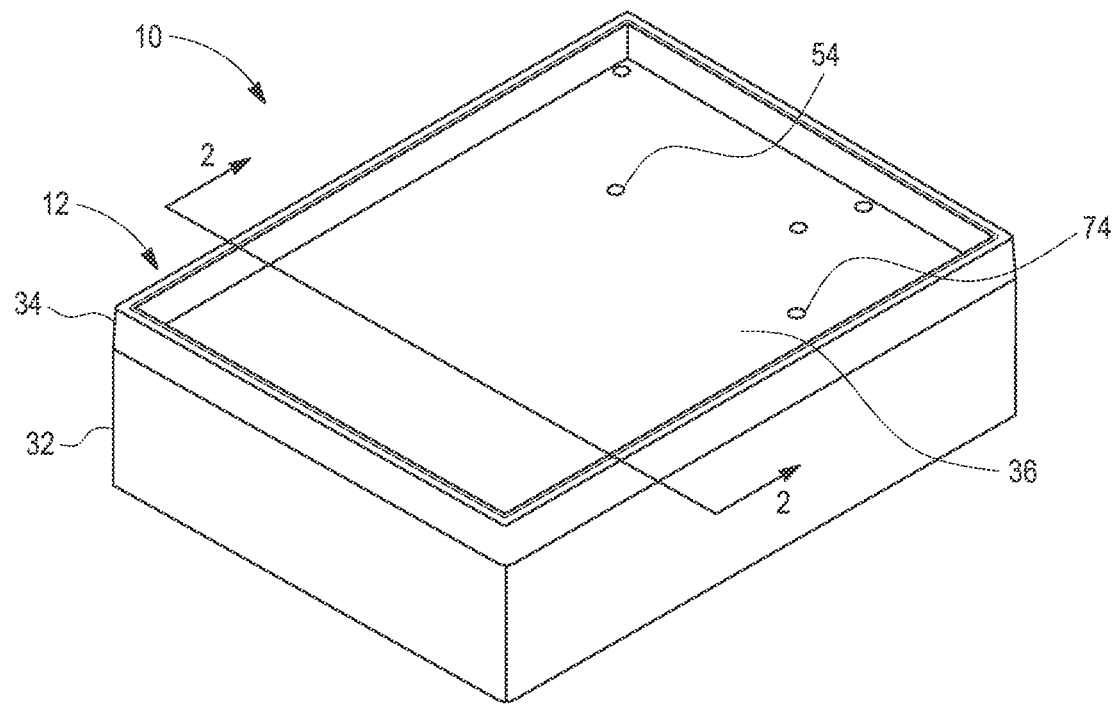
FIG. 1 is a top-left perspective view of a wearable device for automatically injecting medicines into a wearer according to a first embodiment of the present invention, wherein a top cover is removed for clarity.
Figure 2:
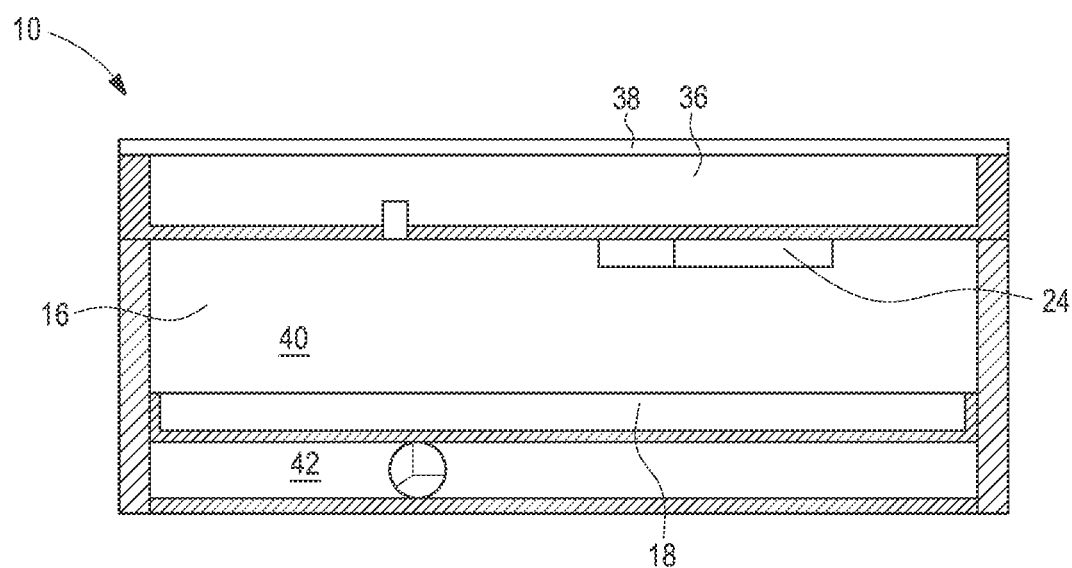
FIG. 2 is a cross-sectional view of the wearable device taken from line 2-2 of FIG. 1, wherein the top cover is shown.
Figure 3:
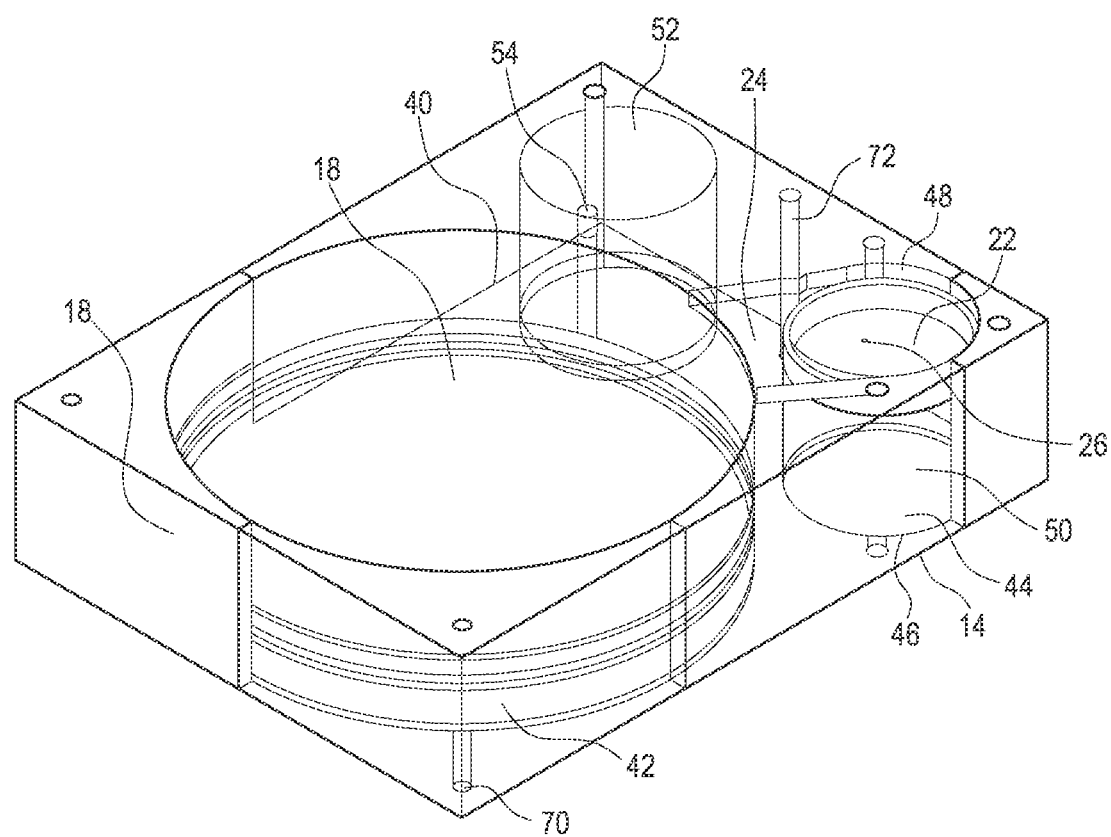
FIG. 3 is a top-left perspective view of the wearable device of FIGS. 1 and 2, wherein an electronic compartment is removed and portions of a main body are transparent for clarity.

FIGS. 1 to 3 illustrate an exemplary wearable device (10) for automatically injecting a fluid into a wearer of the wearable device (10). The fluid is typically a liquid but and is typically a medicine or drug but can alternatively be any other suitable fluid. The illustrated wearable device (10) comprises an enclosure (12), an attachment (14) for securing the enclosure (12) to the wearer, at least one fluid cylinder (16) within the enclosure (12), a fluid piston (18) within the fluid cylinder (16) and configured for longitudinal movement within the fluid cylinder (16), at least one injection cylinder (20) within the enclosure (12), an injection piston (22) within the injection cylinder (20) and configured for longitudinal movement within the injection cylinder (20), a passage (24) connecting the fluid cylinder (16) above the fluid piston (19) with the injection cylinder (20) above the injection piston (22), at least one hypodermic needle (26) carried by the injection piston (22) for insertion into the wearer, a valve member (28) located within the injection cylinder (20) above the injection piston (22) containing the fluid to be injected and blocking flow of the fluid to be injected to the at least one hypodermic needle (26), and at least one tether (30) secured to the valve member (28) to limit movement of the valve member (28) so that the valve member (28) permits flow of the fluid to be injected from the injection cylinder (29) above the injection piston (22) to the at least one hypodermic needle (26) when the injection piston (22) moves a distance adequate to insert the at least one hypodermic needle (26) into the wearer. It is noted that the illustrated wearable device (10) can alternatively have any other suitable configuration as described in more detail hereinbelow.

The illustrated enclosure (12) includes a base portion (32), and top portion (34) closing a top of the base portion (32). The enclosure (12) is sized and shaped to enclose components of the wearable device (10) as described in more detail herein below. The enclosure (12) is preferably sized as small as possible while allowing the wearable device (10) to perform as described herein. The illustrated base portion (32) is generally rectangular shaped having an open top, as described in more detail herein below. The top portion (34) of the enclosure (12) covers and closes the open top of the base portion (32). The illustrated top portion (32) of the enclosure (12) includes an electronics compartment (36) and a cover. (38) The illustrated electronic compartment (36) is sized and shaped to cover the entire top of the base portion (32) to cover and close the base portion (32). The electronic compartment (36) has a cavity with an open top that houses electrical components of the wearable device (10). The cover (38) is sized and shaped to cover the entire open top of the electronic compartment (36) to cover and close the electronic compartment (36). It is noted that the enclosure (12) can be formed of any suitable material or materials. The base portion (32), the electronics compartment (36), and the cover (38) can be secured together in any suitable manner such as for example, but not limited to, mechanical fasteners. It is also noted that the enclosure (12) can alternatively have any other suitable size, shape, and/or configuration.

The illustrated attachment (14) for securing the enclosure (12) to the wearer is a layer of adhesive provided at the bottom surface of the enclosure base portion 32). The adhesive can be pressed against the wearer's skin at a desired location in order to secure the enclosure (12) thereto. The adhesive can be of any suitable type. It is noted that the attachment (14) can alternatively be of any suitable type such as, for example, but not limited to, a strap, belt, sleeve, portion of clothing, clothing, or the like.

The illustrated at least one fluid cylinder (16) is located within the base portion (32) of the enclosure (12) and has an open top end closed by the top portion (34) of the enclosure (12) and a closed bottom end. The illustrated embodiment has a single fluid cylinder (16) that is vertically oriented. The illustrated fluid cylinder (16) is circular in cross-section but can have any other suitable shape to cooperate with the fluid piston (18) therein. The illustrated fluid piston (18) is located within the fluid cylinder (16) and is configured for longitudinal movement in the vertical direction within the fluid cylinder (16). The illustrated fluid piston (18) is disc-shaped and sized to closely match the inner wall of the fluid cylinder (16) to form a fluid tight seal therebetween while allowing movement of the fluid piston (18) within the fluid cylinder (16). The fluid piston (18) can be provided with a seal at its outer edge if desired. The fluid piston (18) divides the fluid cylinder (16) into a first or upper portion or fluid compartment (40) containing the fluid to be injected and a second or lower portion or lower compartment (42). It is noted that the fluid cylinder (16) can alternatively have any other suitable size, shape, and/or configuration.

The illustrated at least one injection cylinder (20) is located within the base portion (32) of the enclosure (12) and having an open top closed by the top portion (34) of the enclosure (12) and an open bottom end closed by a protective membrane (44) selectively piercable by the at least one hypodermic needle (26). The illustrated embodiment has a single injection cylinder (20) that is vertically oriented and parallel with the fluid cylinder (16). The illustrated injection cylinder (20) is circular in cross-section but can have any other suitable shape to cooperate with the injection piston (22) therein. The injection cylinder (20) preferably has a size substantially smaller than the fluid cylinder (16). The illustrated injection cylinder (20) has a diameter about a third of the size of the diameter of the fluid cylinder 916). The illustrated injection piston (22) is located within the injection cylinder (20) and is configured for longitudinal movement in the vertical direction within the injection cylinder (20). A stop ring (46) is provided within the injection cylinder (20) at a bottom of the injector cylinder (20) above the protective membrane (44) to limit downward movement of the injection piston (22). The illustrated injection piston (22) is disc-shaped and sized to closely match the inner wall of the injection cylinder (20) to form a fluid tight seal therebetween while allowing movement of the injection piston (22) within the injection cylinder (20). The injection piston (22) can be provided with a seal at its outer edge if desired. The injection piston (22) divides the injection cylinder (20) into a first or upper portion or injection compartment (48) containing the fluid to be injected and a second or lower portion or needle compartment (50). It is noted that the injection cylinder (20) can alternatively have any other suitable size, shape, and/or configuration.

The illustrated passage (24) connecting the fluid cylinder (16) above the fluid piston (18) with the injection cylinder (20) above the injection piston (22) is in the form of a flow channel extending from a top of the fluid cylinder (16) to a top of the injection cylinder (20). The illustrated flow channel is located at the top of the base portion (32) of the enclosure (12) such that the top of the flow channel is open and closed by the top portion (34) of the enclosure (12). Configured in this manner the fluid to be injected can flow from the fluid cylinder (16) to the injection cylinder (20) through the flow channel. It is noted that the passage (24) can alternatively have any other suitable size, shape, and/or configuration.

Figure 5:
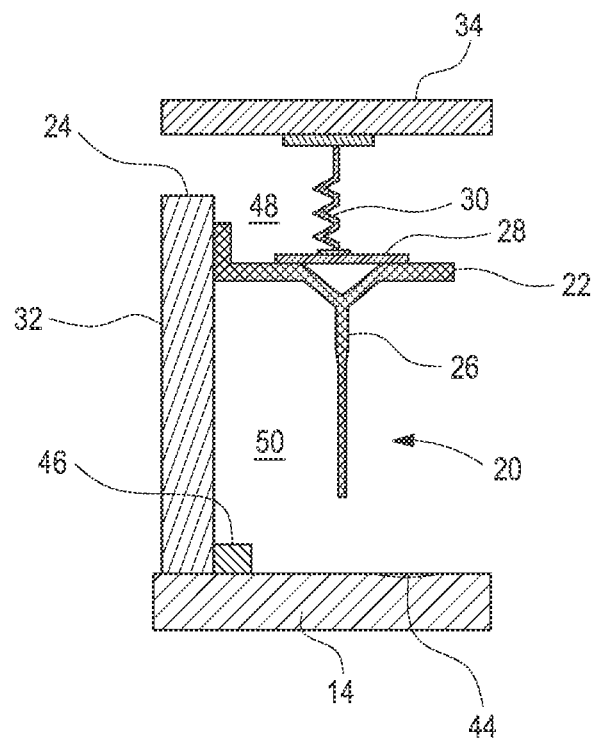
FIG. 5 is an enlarged fragmented view of flow control mechanism of the wearable device of FIGS. 1 to 4.

The illustrated at least one hypodermic needle (26) is secured to and carried by the injection piston (22) for insertion into the wearer (best seen in FIG. 5). The illustrated embodiment includes a single hypodermic needle (26) that downwardly extends from the injection piston (22) into the needle compartment (50) of the injection cylinder (20). The illustrated hypodermic needle (26) extends through the injection piston (22) and has an interior passage that extends entirely through so that the fluid to be injected can pass entirely through the hypodermic needle (26) from the upper end within injection compartment (48) to and out the lower tip of the hypodermic needle (26). It is noted that the at least one hypodermic needle (26) can alternatively have any other suitable size, shape, and/or configuration.

The illustrated embodiment also includes a pressurization system operably connected to the lower compartment (42) of the fluid cylinder (16) for selectively driving the fluid piston (18) in an upward direction. The illustrated pressurization system includes a compressed gas storage compartment (52) within the base portion (32) of the enclosure (12) for holding compressed gas and an electric control valve (54) connecting the compressed gas storage compartment (52) with the lower compartment (42) of the fluid cylinder (16). The compressed gas can be compressed air but any other suitable compressed gas can alternatively be utilized. The control valve (54) is operatively connected to a microcontroller (56) to selectively open and close the control valve (54) to control the flow of compressed gas from the compressed gas storage compartment (52) to the lower compartment (42) of the fluid cylinder (16). It is noted that the pressurization system can alternatively have any other suitable size, shape, and/or configuration. For example, but not limited to, the pressurized gas can be replaced with other energy sources, e.g. combustible chemical, mechanical or other electric sources etc. Also for example, a cartridge style gas container (or other energy source) and drug/injection assembly can be configured for rapid redeployment of the wearable device.

Figure 4:
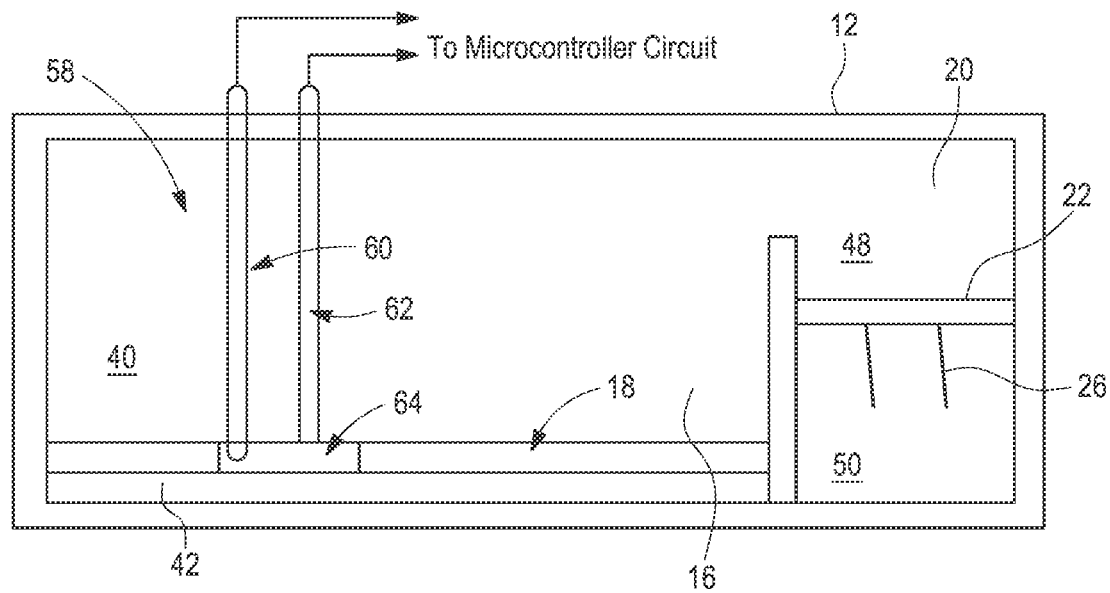
FIG. 4 is a schematic view of a piston position sensor of the wearable device of FIGS. 1 to 3.

As best shown in FIG. 4, the fluid cylinder (16) is preferably provided with a piston position sensor (58). The illustrated piston position sensor (58) provides a continuous analog signal of the position of the fluid piston (18) to the microcontroller (56). The microcontroller (56) can determine the volume of fluid injected using an algorithm and the fluid piston position signal. The illustrated piston position sensor (58) includes vertically extending wires (60) embedded in the wall of the fluid cylinder (16), a vertically extending exposed contact (62) on an inner surface of the fluid cylinder (16), and an exposed conducting surface (64) on an outer edge of the fluid piston (18) sized and shaped to be in contact with the embedded wires (60) and the exposed contact (62) as the fluid piston 9(8) moves upward within the fluid cylinder 916). Upper ends of the embedded wires (60) and the exposed contact (62) are in electrical connection with the circuit of the microcontroller (56). It is noted that the piston position sensor (58) can alternatively have any other suitable configuration.

Figure 4A:
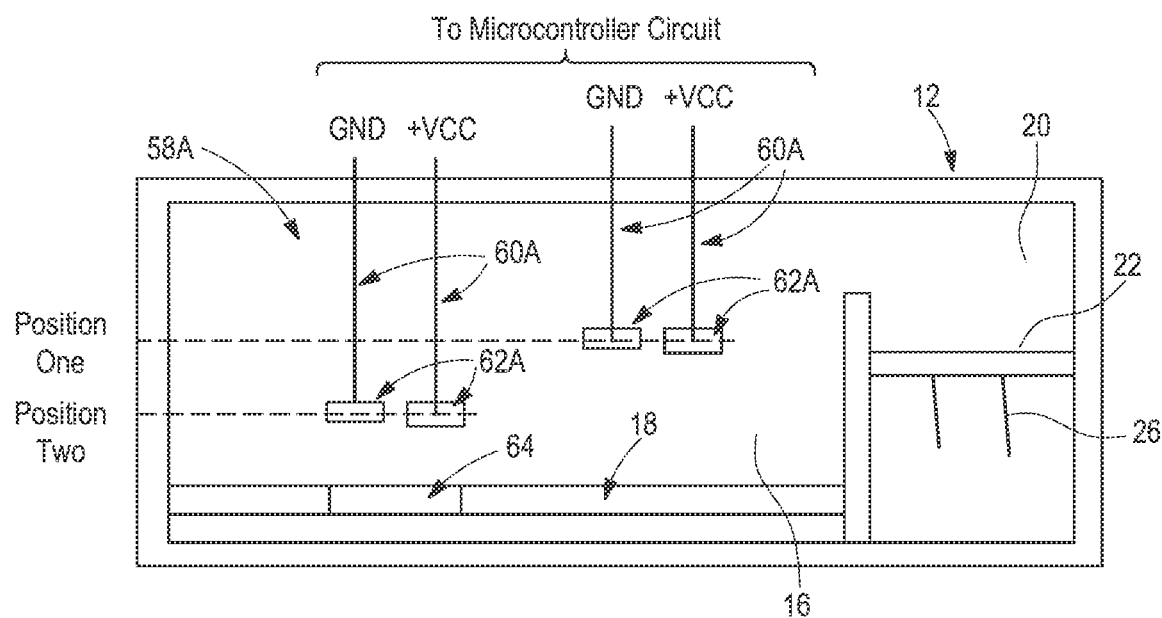
FIG. 4A is a schematic view of an alternative piston position sensor of the wearable device of FIGS. 1 to 3.

As best shown in FIG. 4A discloses an alternative piston position sensor (58A). The illustrated alternative piston position sensor (58A) provides one or more discrete signals of the position of the fluid piston (18) to the microcontroller. The illustrated embodiment includes two discrete positions but one or more than two positions can be utilized. The microcontroller (56) can determine the volume of fluid injected using an algorithm and the fluid piston position signal. The illustrated alternative piston position sensor (58A) includes vertically extending wires (60A) embedded in the wall of the fluid cylinder (16), a pair of laterally spaced-apart exposed contacts (62A) on an inner surface of the fluid cylinder (16) at each position to be sensed, and a conducting surface (64A) on an outer edge of the fluid piston (18) sized and shaped to be in contact with the pair of exposed contacts (62A) as the fluid piston (18) is at one of the discrete positions of the pair exposed contacts (62A). Lower ends of the embedded wires (60A) are each connected to one of the exposed contacts (62A). Upper ends of the embedded wires (60A) are in electrical connection with the circuit of the microcontroller (56). It is noted that the alternative piston position sensor (58A) can alternatively have any other suitable configuration.

As best shown in FIG. 5, the illustrated valve member (28) is located within the injection compartment (48) of the injection cylinder (20) containing the fluid to be injected and blocking flow of the fluid to be injected into the upper or inner end at least one hypodermic needle (26) when the hypodermic needle (26) has not been inserted into the wearer. The illustrated valve member (28) is generally disk shaped and planar. It is noted that if there is more than one hypodermic needle (26), each hypodermic needle (26) can have its own valve member (28). The valve member (28) is preferably formed of a plastic but any other suitable material can alternatively be utilized. It is noted that the valve member (28) can alternatively have any other suitable size, shape and/or configuration.

The illustrated at least one tether (30) is secured between the top of the injection cylinder (20) and the valve member (30) to limit downward movement of the valve member (28) as the injection piston (22) moves downward so that the valve member (28) permits flow of the fluid to be injected from the injection compartment (48) located above the injection piston (22) to the top of the at least one hypodermic needle (26) when the injection piston (22) moves a distance adequate to insert the at least one hypodermic needle (26) into the wearer. The illustrated tether (30) is a flexible strand or filament of plastic. It is noted that the tether (30) can alternatively be made of any other suitable material. The tether (30) is preferably folded, coiled, elastic or the like so that the valve member (28) remains closed as the injection piston (22) is moved downward within the injection cylinder (20) until the hypodermic needle (26) is at least partially inserted into to skin of the wearer. It is noted that the tether (30) can alternatively have any other suitable size, shape and/or configuration.

Figure 6:
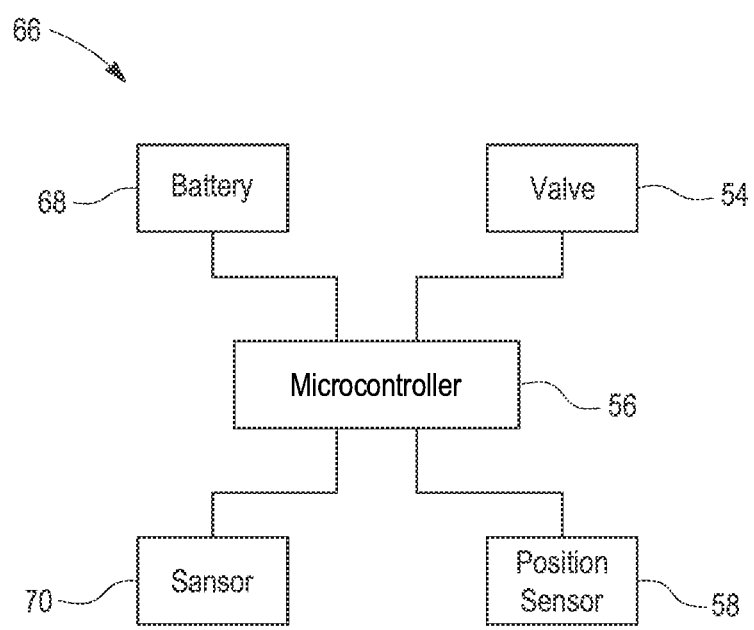
FIG. 6 is a block diagram of and electronic system of the wearable device of FIGS. 1 to 5.

FIG. 6 shows a block diagram of the control system (66) for the illustrated wearable device (10). The micro controller (56) is in communication with a battery (68) for powering components requiring electrical power, the control valve (54) of the pressurization system for opening and closing the control valve (54), the piston position sensor (58, 58A) for determining the amount of fluid injected into the wearer, and at least one sensor or electrode (70) for receiving biometric data regarding the wearer. The at least one sensor or electrode (70) is embedded in the bottom of the base portion (32) of the enclosure (12). Wires from the at least one sensor (70) extend upward through passages (72) to the top of the base portion (32) and though openings (74) in the electronics compartment (36) to the circuit of the microcontroller (56) located therein. The at least one sensor (70) provides biometric data to the microcontroller (56) and the microcontroller (56) utilizes the biometric feedback for controlling the control valve (54) using smart control algorithms running on the microcontroller (56), thus controlling the rate of drug injection. The microcontroller (56) is provided with a suitable processor, memory, and algorithms for controlling operation of the wearable device (10) as described herein. It is noted that the control system (66) can alternatively have any other suitable configuration.

Figure 7:
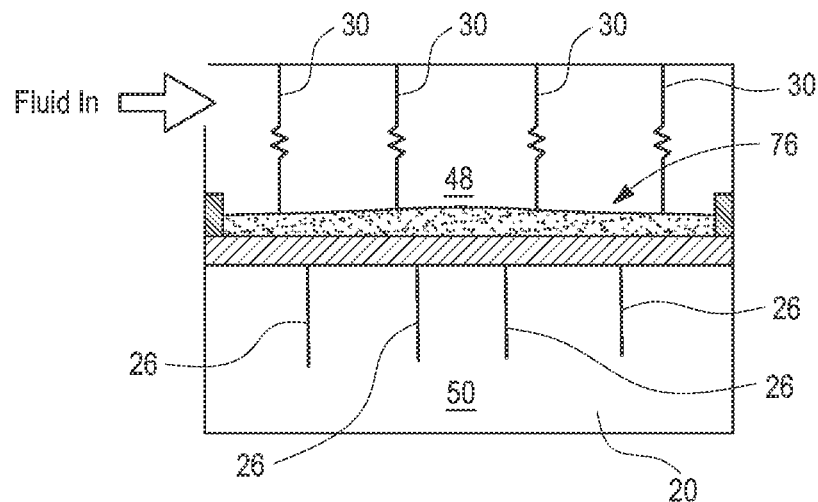
FIG. 7 is schematic view of an alternative flow control mechanism of the wearable device of FIGS. 1 to 6.
Figure 7A:
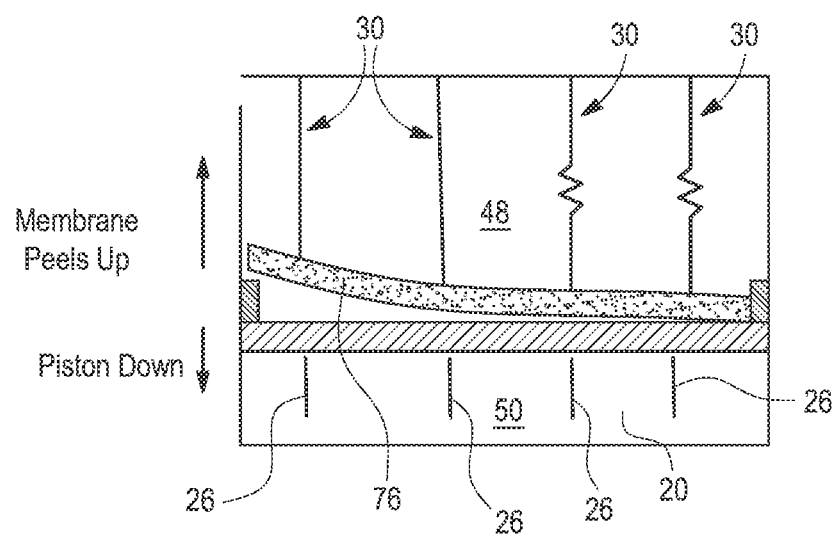
FIG. 7A is a schematic view of the alternative flow control mechanism of FIG. 7, wherein the injection piston has moved to a lower position.
Figure 7B:
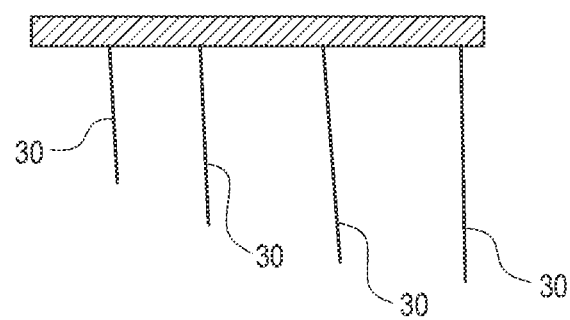
FIG. 7B is a schematic view of the alternative flow control mechanism of FIGS. 7 and 7A, showing all tethers fully extended It should be understood that the appended drawings are not necessarily to scale, presenting a somewhat simplified representation of various preferred features illustrative of the basic principles of the invention. The specific design features of the wearable devices as disclosed herein, including, for example, specific dimensions and shapes of the various components will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the storage compartment support systems illustrated in the drawings. In general, up or upward refers to an upward direction generally within the plane of the paper in FIG. 4 and down or downward refers to a downward direction generally within the plane of the paper in FIG. 4. Also in general, forward or front refers to a direction extending out the plane of the paper in FIG. 1 and back or rear refers to a direction extending into the plane of the paper in FIG. 1.

FIGS. 7, 7A, and 7B illustrate a variation of the wearable device 910) wherein there is a plurality of the hypodermic needles (26) and a single valve member (28) in the form of a flexible membrane seal (76) secured by a plurality of tethers (30). The illustrated plurality of hypodermic needles (26) can be spaced apart along the circular injection piston (22) in an suitable manner. The illustrated flexible membrane seal (76) is sized to cover and block all of the fluid openings for the plurality hypodermic needles (26) and is secured to the top of injection cylinder (20) by a plurality of tethers (30) to operate substantially the same as described hereinabove. However, the illustrated tethers (30) are provided with increasing lengths (best shown in FIG. 7B) from one side to the other so that the flexible membrane seal (76) first peals up from one side until it is entirely removed from the openings to the hypodermic needles (26). This decreases the chance that the flexible membrane seal (76) undesirably adheres to the top of the injection piston (22). The flexible membrane seal (76) is preferably formed of a plastic but any other suitable material can alternatively be utilized.

In operation, the wearable device (10) is secured to the skin of the wearer at a desired location using the adhesive layer (14). The sensor (70) monitors the wearer's physiological parameters and when the microcontroller (56) determines there is an event necessitating administration of the medication, the microcontroller (56) activates a trigger. Upon trigger by the microcontroller (56), the control valve (54) is opened by the microcontroller (56) and the compressed air enters the lower compartment (42) of the fluid cylinder (16) pushing the fluid piston (18) upward and thus pushing the injection piston (22) downward. The valve member (28) prevents fluid flow through the hypodermic needle (26) until the hypodermic needle (26) is fully inserted into the tissue of the wearer. At this stage, movement of the valve member (28) is halted is halted by the tether (tether) so that the valve member (38) is disengaged from the injection piston (22) and the drug flows into the tissue of the wearer through the hypodermic needle (26). Further entry of compressed gas into lower compartment (42) of the fluid cylinder (16) pushes the injection piston (18) downward to inject fluid through hypodermic needle (26) into the tissue. The injection piston (22) stops moving when it engages the stop ring (46) within the injection cylinder (18).

The relative movement of the pistons (18, 22) and the valve member (28) is controlled by the microcontroller (56) and/or other smart electrically activated polymer (EAP) based structures/smart structures, piston and/or seals. The piston position sensor (58, 58A) provides feedback control by which final injection rate and profile is controlled by the microcontroller (56). An algorithm run by the microcontroller (56) controls the control valve (54) to provide a preprogrammed drug flow rate.

As stated hereinabove, the wearable device (10) is intended to treat a specific condition. Drug administration is tailored to treat the catastrophic event, and drug administration is driven by the sensor (70) that detects the wearer's physiological changes that are associated with, and reliably predict the emergency. In the case of treating opioid overdoses, the wearable device (10) is small enough (2 cm×2 cm×1 cm with a volumetric capacity of 1 cubic centimeters) to be worn almost anywhere such as, for example, the arm, any extremity, or the abdomen. The dimensions of the wearable device (10) can be adjusted for each specific use case.

To illustrate a possible application of the wearable device (10), the wearable device (10) may be worn by an at-risk heroin addict or recreational drug user to treat an opioid overdose. The sensor (70), in this case would be an oximeter that is programmed to respond to a specific, reduced level of oxygen tension in the wearer's blood, which in this setting would predict an opioid overdose. When the predetermined level of reduced oxygen is registered from the signal of the sensor (70), the microcontroller (56) of the fluid cylinder (15) would trigger a sequence of events that involves entry of gas into the fluid compartment (42), which in turn creates pressure on the injection assembly and drives the hypodermic needle (26) into the underlying subcutaneous tissue. Continued pressure then promotes the release of a specific volume (i.e. 1 cubic centimeter) of the antidote (e.g., nalmefene) into the hypodermic needle (26) and then the victim's subcutaneous tissue. The microcontroller (56) would be programmed to trigger a second injection of cubic centimeter of antidote (e.g., nalmefene) independent of the oxygen tension thereafter to ensure adequate treatment of the putative overdose.

Any of the features or attributes of the above-described embodiments and variations can be used in combination with any of the other features and attributes of the above-described embodiments and variations as desired.

From the foregoing disclosure it will be apparent that the illustrated smart wearable devices for automatically injecting medicines deliver medicines on-demand and without human intervention. It is also apparent that these wearable devices store drugs until needed, and upon activation insert hypodermic needles to sterilely deliver a pre-set volume of drug into the wearer's subcutaneous tissue. Additionally it is apparent that the wearable devices can deliver one or more time dependent stages once activated with a single intervention, can be connected to a physiological monitoring system for automatic activation without human intervention, can be activated remotely by health professionals or others monitoring physiological metrics, and that infections are eliminated because the needles are only deployed when triggered. Furthermore, it is apparent that the wearable devices are extremely compact, unobtrusive and convenient to wear for long periods of time. Moreover, the smart wearable devices can be used in many different applications including, but not limited to, defense applications in which soldiers utilize smart the smart wearable devices to inject pain killers, and/or antidotes to chemical or biological agents.

From the foregoing disclosure and detailed description of certain preferred embodiments, it will be apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A wearable device for automatically injecting a fluid into a wearer of the wearable device, the wearable device comprising, in combination:
   an enclosure;
   an attachment for securing the enclosure to the wearer;
   an injection cylinder within the enclosure;
   an injection piston within the injection cylinder configured for movement within the injection cylinder;
   at least one hypodermic needle carried by the injection piston for insertion into the wearer;
   wherein the injection piston divides the injection cylinder into a first portion containing the fluid to be injected and a second portion containing an insertion end of the at least one hypodermic needle;
   a valve member located within the first portion of the injection cylinder containing the fluid to be injected and blocking flow of the fluid to be injected to the at least one hypodermic needle; and
   at least one tether secured to the valve member to limit movement of the valve member so that the valve member permits flow of the fluid to be injected from the injection cylinder above the injection piston to the at least one hypodermic needle when the injection piston moves a distance adequate to insert the at least one hypodermic needle into the wearer.

2. The wearable device according to claim 1, wherein the attachment includes a layer of adhesive on an outer surface of the enclosure.

3. The wearable device according to claim 1, wherein the tether is a flexible filament.

4. The wearable device according to claim 1, wherein there is only one at least one tether and only one at least one hypodermic needle.

5. The wearable device according to claim 1, wherein there is a plurality of the at least one hypodermic needle.

6. The wearable device according to claim 1, wherein there is a plurality of the at least one tether secured to the valve member.

7. The wearable device according to claim 6, wherein the valve member is a membrane seal and the plurality of the at least one tether secured to the valve member have different lengths to peel the valve member off of the injection piston as the injection piston moves away from the valve member.

8. The wearable device according to claim 7, wherein there is a plurality of the at least one hypodermic needle.

9. The wearable device according to claim 1, further comprising at least one position sensor for determining the position of the injection piston within the injection cylinder.

10. The wearable device according to claim 1, further comprising a fluid cylinder parallel with the injection cylinder, a fluid piston movable within the fluid cylinder, and a passage between the fluid cylinder and the injection cylinder with the fluid to be injected located between the fluid piston and the injection piston so that initial movement of the fluid piston moves the injection piston to insert the at least one hypodermic needle into the wearer and further movement of the fluid piston drives the fluid to be injected into the at least one hypodermic needle to inject the fluid into the wearer.

11. A wearable device for automatically injecting a fluid into a wearer of the wearable device, the wearable device comprising, in combination:
- an enclosure including a base portion, and top portion closing a top of the base portion;
- an attachment for securing the enclosure to the wearer;
- a fluid cylinder within the base portion of the enclosure and having an open top closed by the top portion of the enclosure;
- an injection cylinder within the base portion of the enclosure and having an open top closed by the top portion of the enclosure;
- a fluid piston within the fluid cylinder configured for longitudinal movement within the fluid cylinder;
- an injection piston within the injection cylinder configured for longitudinal movement within the injection cylinder;
- a passage connecting the fluid cylinder above the fluid piston with the injection cylinder above the injection piston;
- at least one hypodermic needle carried by the injection piston for insertion into the wearer;
- wherein the injection piston divides the injection cylinder into a first portion containing the fluid to be injected and a second portion containing an insertion end of the at least one hypodermic needle;
- wherein the fluid piston divides the fluid cylinder into a first portion containing the fluid to be injected and a second portion;
- a valve member located within the first portion of the injection cylinder containing the fluid to be injected and blocking flow of the fluid to be injected to the at least one hypodermic needle; and
- at least one tether secured to the valve member to limit movement of the valve member so that the valve member permits flow of the fluid to be injected from the injection cylinder above the injection piston to the at least one hypodermic needle when the injection piston moves a distance adequate to insert the at least one hypodermic needle into the wearer.

12. The wearable device according to claim 11, wherein the top portion includes an electronics compartment covering the top of the base portion and a cover covering a top of the electronics compartment.

13. The wearable device according to claim 11, wherein the fluid cylinder is parallel with the injection cylinder.

14. The wearable device according to claim 11, wherein the passage is a channel having an open top formed in the top of the base portion of the enclosure and the open top of the channel is closed by the top portion of the enclosure.

15. The wearable device according to claim 11, wherein there is a plurality of the at least one hypodermic needle and wherein the valve member is a flexible membrane seal.

16. The wearable device according to claim 11, wherein the attachment includes a layer of adhesive on an outer surface of the enclosure.

17. The wearable device according to claim 11, further comprising at least one position sensor for determining the position of the injection piston within the injection cylinder.

18. The wearable device according to claim 11, wherein there is a plurality of the at least one hypodermic needle.

* * * * *